United States Patent
Kato

Patent Number: 5,901,391
Date of Patent: May 11, 1999

[54] BED

[75] Inventor: Makoto Kato, Hamamatsu, Japan

[73] Assignee: Hamamatsu Photonics K.K., Hamamatsu, Japan

[21] Appl. No.: 08/857,901

[22] Filed: May 16, 1997

[30] Foreign Application Priority Data

Jun. 13, 1996 [JP] Japan .................. 8-152667

[51] Int. Cl.⁶ .................................. A47C 27/08
[52] U.S. Cl. ........................... 5/666; 5/665; 5/905
[58] Field of Search ................. 5/665, 666, 655.5, 5/422, 905, 308; 362/130

[56] References Cited

U.S. PATENT DOCUMENTS

| | | | |
|---|---|---|---|
| 3,085,568 | 4/1963 | Whitesell | 5/422 |
| 3,585,356 | 6/1971 | Hall | 5/422 |
| 3,746,835 | 7/1973 | Yu et al. | 5/422 |
| 4,461,278 | 7/1984 | Mori | 126/440 |
| 4,602,396 | 7/1986 | Fraige | 5/451 |
| 4,742,437 | 5/1988 | Downey | 5/666 |
| 4,807,315 | 2/1989 | Wachenheim | 5/308 |
| 4,825,868 | 5/1989 | Susa et al. | 128/376 |
| 5,010,608 | 4/1991 | Barnett et al. | 5/453 |
| 5,695,455 | 12/1997 | Alton, Jr. et al. | 5/666 |

FOREIGN PATENT DOCUMENTS 2500921  3/1996  Japan .

*Primary Examiner*—Kenneth J. Dorner
*Assistant Examiner*—Fredrick Conley
*Attorney, Agent, or Firm*—Pillsbury Madison & Sutro LLP

[57] ABSTRACT

A bed includes a bag filled with a transparent fluid and formed with a transparent portion at least at an upper surface portion thereof, and a light source for emitting light. The light emitted from the light source passes through the fluid and propagates to an outside of the bag through the transparent portion on an upper surface of the bag. As a result, a bedsore can be prevented, and a decrease in bone mass can be prevented, thus suppressing occurrence of osteoporosis.

13 Claims, 5 Drawing Sheets

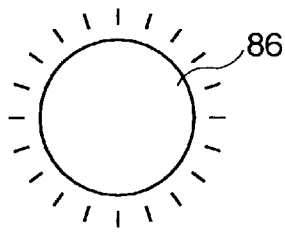
*Fig.6*
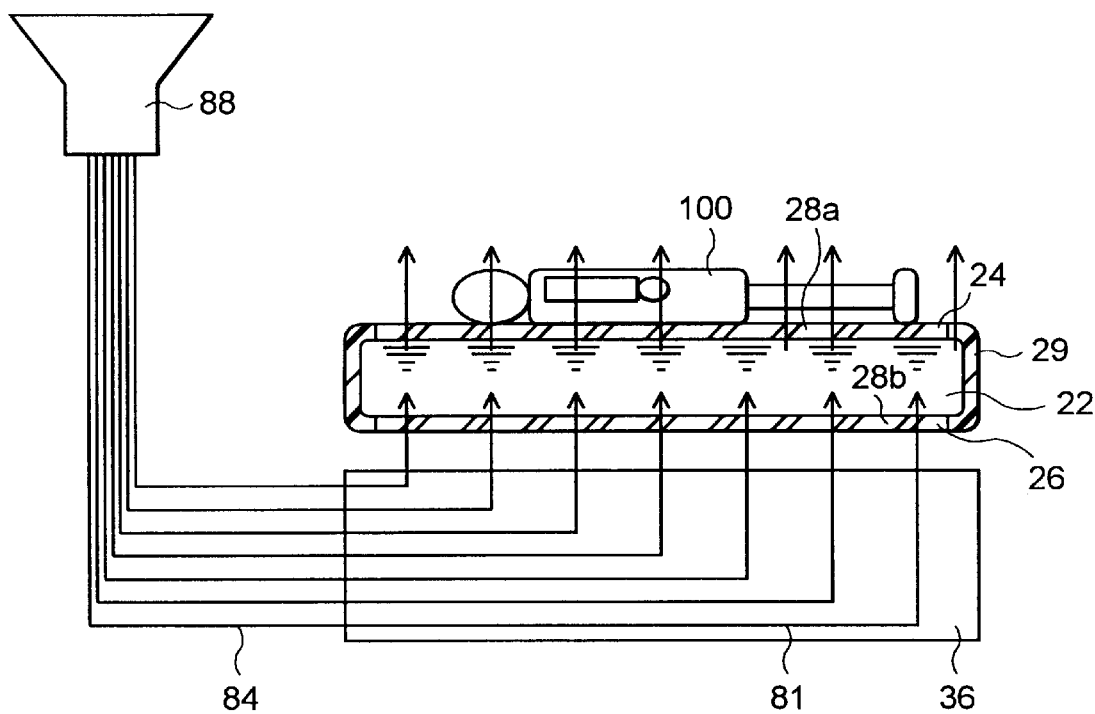
*Fig.7*
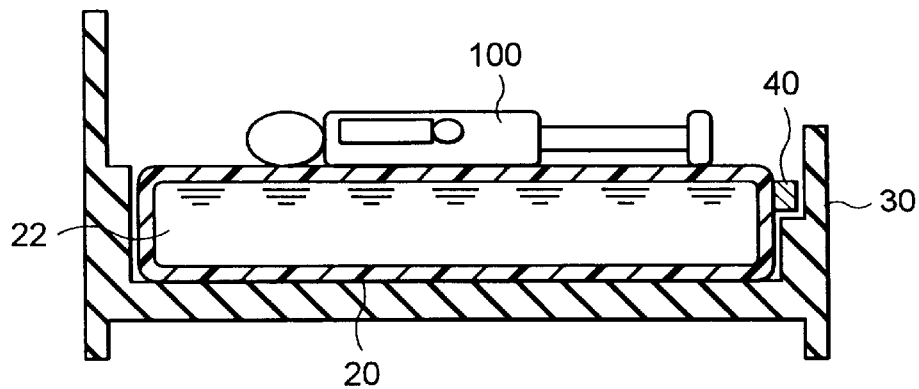

BED

BACKGROUND OF THE INVENTION

1. Field of the Invention

The present invention relates to a bed and, more particularly, to a bed used in, e.g., medical applications and the like.

2. Related Background Art

People who are confined to bed from various reasons rarely move their bodies and thus tend to cause bedsores. A bedsore refers to a necrotic state that occurs to a skin or soft tissue of a portion, where a bone projects, of a patient who is confined to bed for a long period of time, as a result of circulatory malady when the skin or tissue is pressed between the bone and the bed over a long period of time.

For example, a water bed 1 is conventionally used to prevent a bedsore. In the water bed 1, as shown in FIG. 7, a water bag 20 filled with water 22 is supported by a bed frame 30. A heater 40 having a thermostat is attached to the side portion of the water bag 20. When a bed user 100, e.g., a patient who is confined to bed, lies on the water bed 1, a uniform force acts on the contact portion of the water bag 20 and the bed user 100, so that no bedsore occurs easily. In addition, the bed user 100 can sleep comfortably.

However, as the causes of bedsore, in addition to the pressure described above, bacterial infection must not be forgotten. Therefore, currently, a bedsore is prevented by, e.g., cleaning a bed-confined patient with alcohol by a person in charge of nursing.

In the bed-confined state, a decrease in bone mass occurs to the bed user 100. When the bone mass decreases, porosity occurs in the bone likely to cause osteoporosis finally. As a result, the patient tends to suffer a fracture during care, which will cause bed confinement in turn, leading to a vicious cycle.

It is said that, at present, there are 4 million people in Japan who are confined to bed. As the percentage of aged people increases in the future, the number of bed-confined patients will increase, leading to an increase in medical cost.

SUMMARY OF THE INVENTION

The present invention has been made in order to solve the problems described above, and has as its object to obtain a bed that can prevent a bedsore and a decrease the bone mass, thus suppressing occurrence of osteoporosis.

An aspect of the present invention, there is provided a bed comprising:
- a bag filled with a transparent fluid, having a flexibility at least at an upper surface portion thereof, and formed with a transparent portion;
- a bed frame for holding the bag;
- a light source for emitting light; and
- a power supply for supplying power to the light source;
- wherein the light emitted from the light source passes through the fluid and propagates outside the bag through the transparent portion on the upper surface of the bag.

The other aspect of the present invention, there is provided a bed comprising:
- a bag filled with a transparent fluid, having a flexibility at least at an upper surface portion thereof, and formed with a transparent portion;
- a bed frame for holding the bag;
- condensing means for condensing natural light; and
- light-transmitting means for transmitting light condensed by the condensing means;
- wherein the light transmitted from the light-transmitting means passes through the fluid and propagates outside the bag through the transparent portion on an upper surface of the bag.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

BRIEF DESCRIPTION OF THE DRAWINGS

FIG. 1 is a schematic perspective view showing a bed according to the first embodiment of the present invention and used in medical applications and the like;

FIG. 6 is a schematic side sectional view showing a bed according to the forth embodiment of the present invention; and FIG. 7 is a schematic side sectional view showing a conventional water bed.

DESCRIPTION OF THE PREFERRED EMBODIMENTS

A bed according to the preferred embodiments of the present invention will be described with reference to the accompanying drawings.

Figure 1:
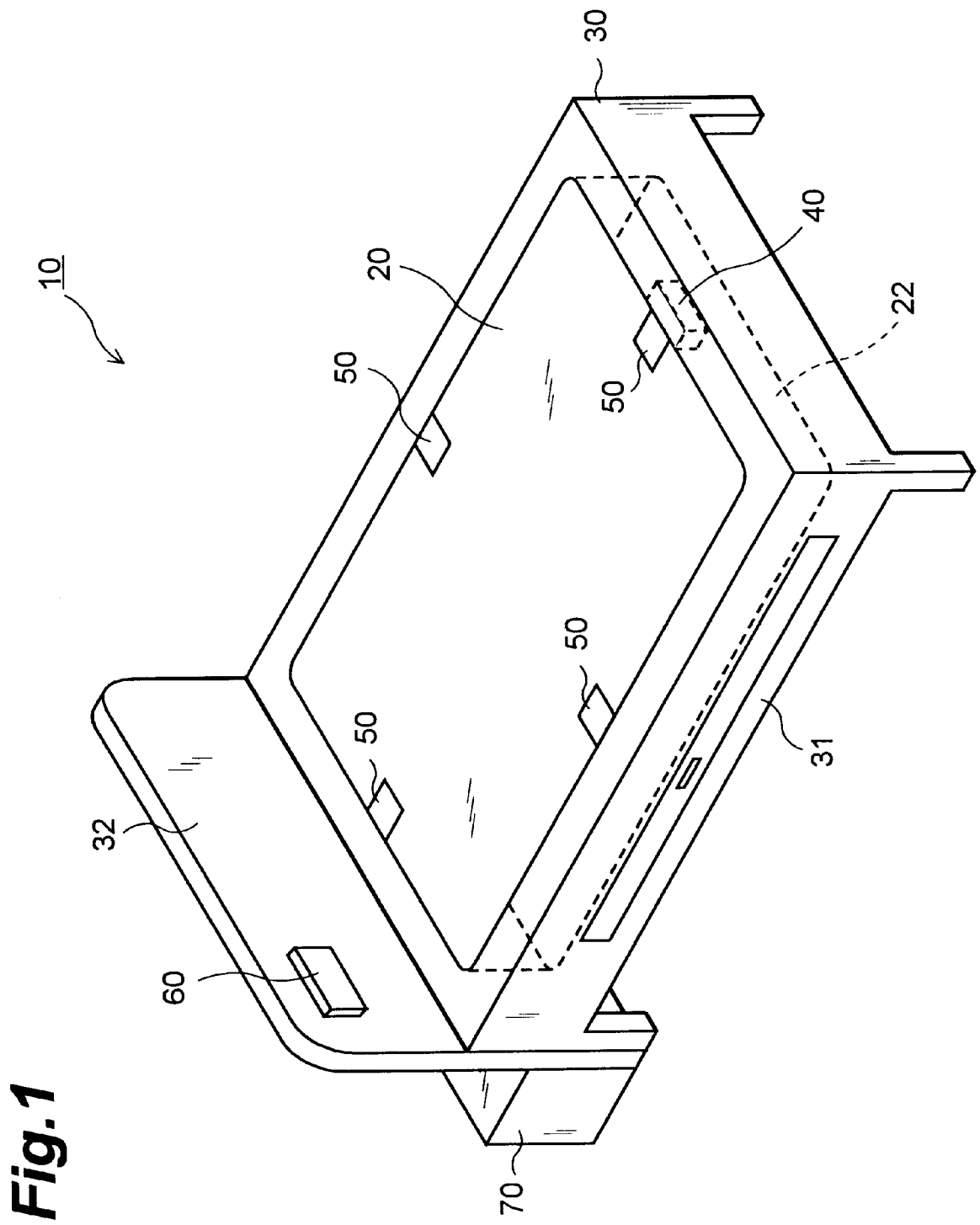

FIG. 1 is a schematic perspective view showing a bed according to the first embodiment of the present invention. In this bed 10, a water bag 20 filled with water 22 is supported by a bed frame 30. A heater 40 having a thermostat is fixed to the side portion of the water bag 20. The water 22 in the water bag 20 is held at a desired temperature by this heater 40. Optical sensors 50 comprising semiconductors are fixed to an upper surface portion 24 of the water bag 20, and a controller 60 having a switch is fixed to a back rest portion 32 of the bed frame 30 (both will be described in detail later). A power supply 70 is arranged outside the bed 10.

Figure 2:
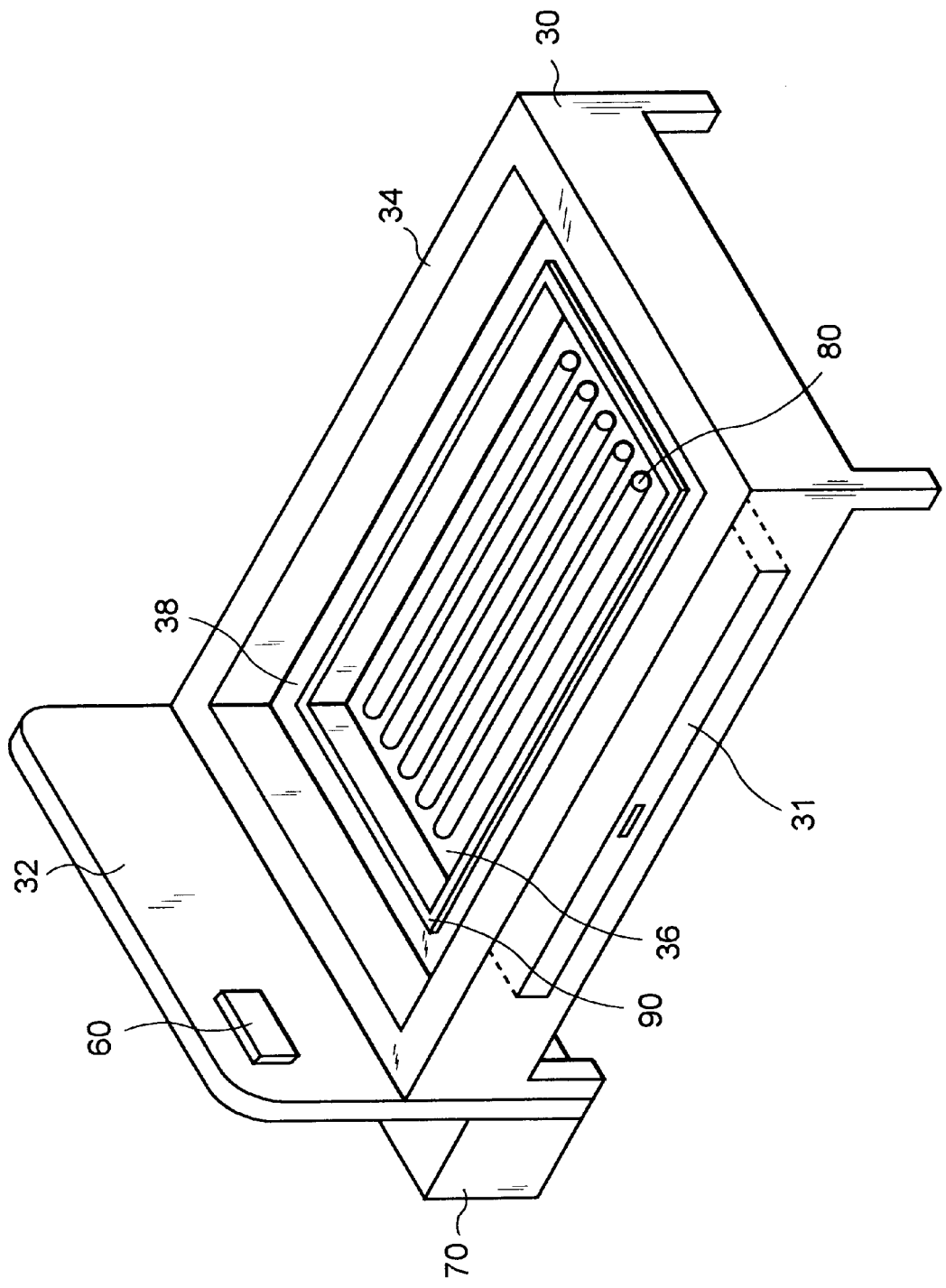
FIG. 2 is a schematic perspective view of the bed shown in FIG. 1 from which a water bag and the like are removed.

FIG. 2 is a schematic perspective view of the bed 10 shown in FIG. 1 from which the water bag 20, the heater 40 having the thermostat, and the like are removed. Referring to FIG. 2, a bed portion 34 of the bed frame 30 has a stepped shape, and a lower stage portion 36 and a middle stage portion 38 are formed inside the bed portion 34. Light emitters 80 comprising, e.g., fluorescent lamps, that emit near ultraviolet rays are disposed on the lower stage portion 36 to be parallel to the longitudinal direction of the bed portion 34. A transparent protection plate 90 is arranged on the middle stage portion 38 to impart mechanical strength, so that the load of the water bag 20 will not be applied to the light emitters 80. Although the light emitters 80 are arranged in the same direction as the longitudinal direction of the bed portion 34, they may be arranged in a direction perpendicular to the longitudinal direction of the bed portion 34. In this case, short-size light emitters suffice, which is advantageous in terms of cost. The light emitters 80 are not limited to fluorescent lamps but can be a surface light emitter, e.g., an EL panel.

Preferably, a drawer 31 having guide rails may be mounted in the bed frame 30, and light emitters 80 identical to those described above may be arranged in the drawer 31. With this arrangement, if the service life of the light emitters 80 expires and the light emitters 80 must thus be exchanged, they can be easily exchanged by withdrawing and storing the drawer 31. Also, the state of the light source can be observed easily, and the light source can be maintained easily.

Figure 3:
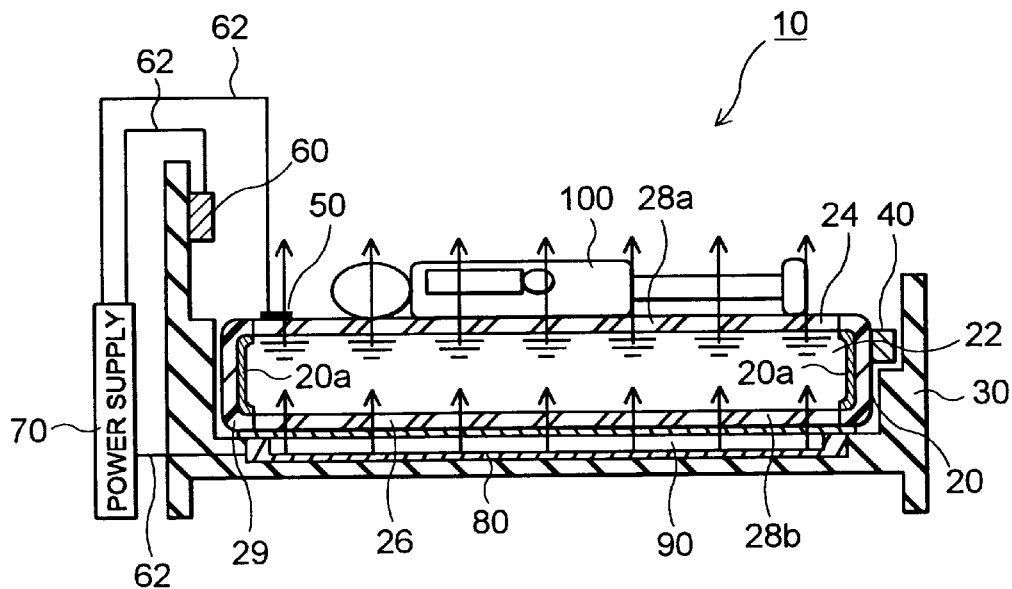
FIG. 3 is a schematic side sectional view for explaining the operation of the bed according to the first embodiment of the present invention.

FIG. 3 is a schematic side sectional view of the bed 10 shown in FIG. 1. Referring to FIG. 3, a transparent portion 28a made of a transparent material is formed at least at the upper surface portion 24 of the water bag 20. In FIG. 3, a transparent portion 28b is formed in a lower surface portion 26 as well. Except for these portions, an opaque portion 29 made of an opaque material is formed. As the material of the transparent portions 28a and 28b, a translucence member having flexibility is preferable in order to support the weight of a bed user 100 with a larger number of contact portions when he lies on the bed 10. For example, a vinyl chloride-based material or a rubber-based material can be suitably used, and a reinforcing member, e.g., fibers, may be used together with the flexible material.

The light emitters 80 are connected to the power supply 70 through an electric lead 62. The power supply 70 is connected to the controller 60 having the switch and to an optical sensor 50 through other electric leads 62. The heater 40 having the thermostat is also connected to the power supply 70 through an electric lead (not shown). The power supply 70 need not be arranged outside the bed 10 but may be incorporated in the bed frame 30 so that it is integrated with the bed 10. The optical sensors 50 need not be fixed on the upper surface portion 24 of the water bag 20, but optical fibers (not shown) may be fixed on the upper surface portion 24. Light may be output from these optical fibers and detected by optical sensors 50 arranged outside the bed 10.

The operation of the bed according to the first embodiment of the present invention will be described.

To use this bed 10, first, the controller 60 having the switch is turned on to supply the current from the power supply 70 to the heater 40 having the thermostat. The water 22 in the water bag 20 is heated to a predetermined temperature by the heater 40 having the thermostat in accordance with natural convection. When the current from the power supply 70 is supplied to the light emitters 80 by the controller 60 having the switch, the light emitters 80 fixed to the lower stage portion 36 of the bed frame 30 emit near ultraviolet rays, as indicated by arrows in FIG. 3. The emitted near ultraviolet rays pass through the transparent portion 28b, the water 22, and the transparent portion 28a and are radiated to the outside of the bed 10 through the upper surface of the water bag 20 efficiently. At this time, the opaque portion 29 constituting the water bag 20, i.e., the portion other than the upper surface portion 24 and lower surface portion 26, may form a high-reflectance member made of a high-reflectance material. Alternatively, the inner surface of the opaque portion 29 may be covered with a high-reflectance film 20a or the like. For example, the reflection efficiency can be increased by forming a metal film on the inner surface of the opaque portion 29 by vapor deposition or by providing a mirror or reflection plate on the inner surface of the opaque portion 29, thereby increasing the amount of light emerging from the transparent portion 28a.

A light-diffusing agent (not shown) for diffusing light may be dispersed into the water 22 in the water bag 20. As the light-diffusing agent, for example, a soap component, an emulsifying agent, small balls of foamed styrene, or the like may be used. In this case, the non-uniformity in radiation of light emerging from the transparent portion 28a is decreased so that uniform light can be obtained from the transparent portion 28a.

Light emitted from the transparent portion 28a of the upper surface portion 24 is detected by the optical sensors 50. Detection signals from the optical sensors 50 are output to the controller 60 having the switch through the power supply 70. The controller 60 having the switch outputs to the power supply 70 a control signal for adjusting the light to have a light amount which does not adversely affect the human body. Alternatively, the light amount can be arbitrarily changed by using the controller 60 having the switch in accordance with the preference of the bed user 100. Based on this control signal, power is supplied from the power supply 70 to the light emitters 80 through the electric lead. If the bed user 100 feels the light too glaring, the use of an eye mask or the like is desirable.

When, e.g., a bed-confined patient, lies as the bed user 100 on the upper surface portion 24 of the water bag 20 in this state, not only he can sleep comfortably, but also a bedsore caused by bacterial infection is prevented, because the radiated light has a bactericidal action against bacteria present between the upper surface portion 24 of the water bag 20 and the patient. As a result, the number of times of disinfection done by the person in charge of nursing who attends to the bed-confined person can be decreased.

Near ultraviolet rays emitted from the light emitters 80 can cause generation of active vitamin D that cannot be generated in the human body. Active vitamin D plays an important role in generation of the bone. The bed 10 according to the present invention can simulate a sunbath. Therefore, when, e.g., a bed-confined person who rarely has an opportunity to sunbathe lies on the bed 10, active vitamin D is generated in the patient's body, thereby suppressing progress of osteoporosis.

In this embodiment, the light emerging from the light emitters 80 is near ultraviolet rays. However, the present invention can also be applied to a thermotherapy by using infrared rays. It is a matter of course that the bed of the present invention can also be effectively used in applications other than medical applications, e.g., a suntan salon and the like.

Figure 4:
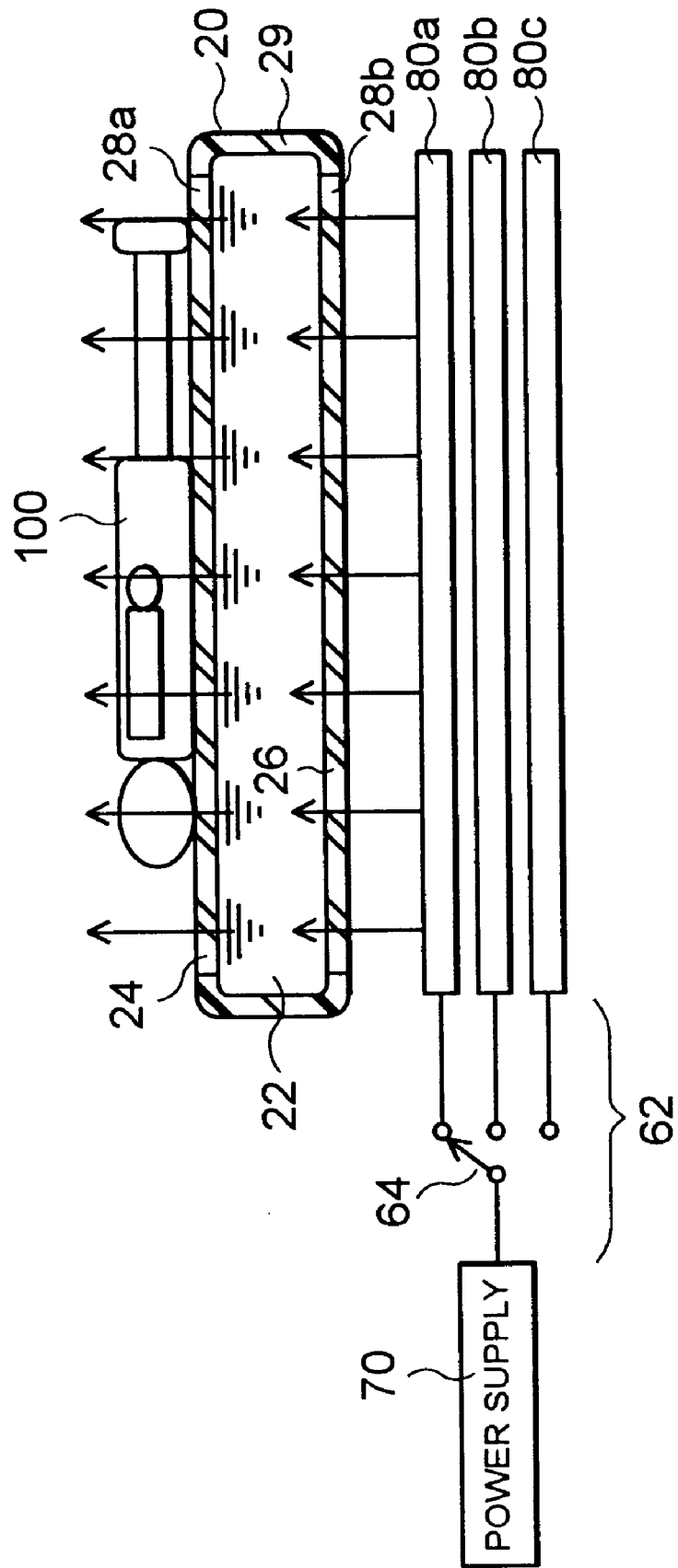
FIG. 4 is a schematic side sectional view showing a bed according to the second embodiment of the present invention.

FIG. 4 is a schematic side sectional view showing a bed according to the second embodiment of the present invention. In FIG. 4, a bed frame, a bed portion, and the like are omitted from illustration. The bed shown in FIG. 4 is different from that of the first embodiment in that a plurality of light emitters 80a to 80c for emitting rays having different wavelengths are provided on a lower stage portion 36 of a bed frame 30. A power supply 70 is connected to a switching means 64 that connects the power supply 70 to either one of the light emitters 80a to 80c. Regarding optical sensors, ones capable of detecting rays corresponding to the types of the light emitters 80a to 80c are provided (not shown).

In this embodiment, the plurality of light emitters 80a to 80c having different wavelengths can be selectively used. For example, sterilization and synthesis of active vitamin D may be performed with near ultraviolet rays, and thereafter a light emitter for emitting infrared rays may be used in turn to perform a thermotherapy.

Figure 5:
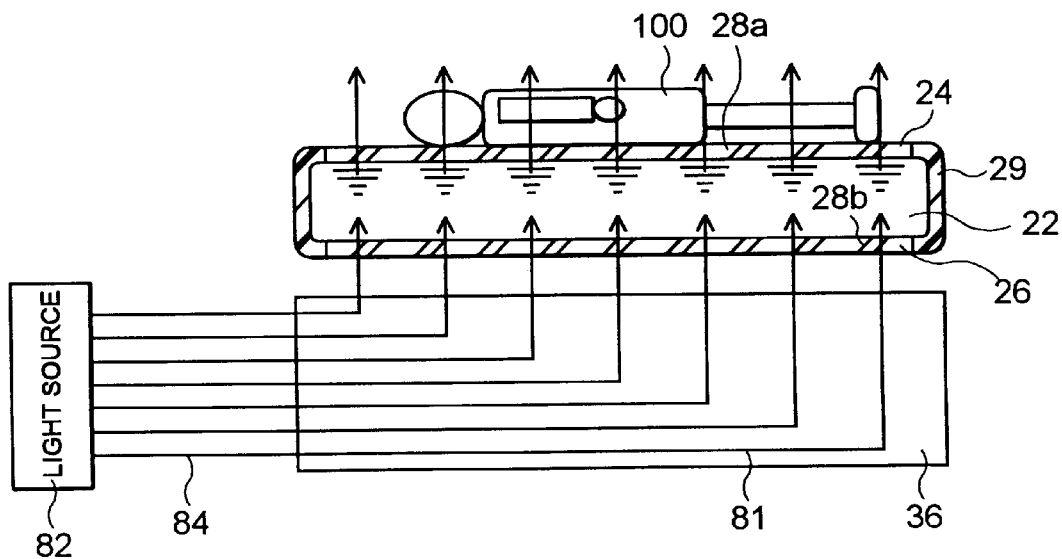
FIG. 5 is a schematic side sectional view showing a bed according to the third embodiment of the present invention.

FIG. 5 is a schematic side sectional view showing a bed according to the third embodiment of the present invention. In FIG. 5, a bed frame, a bed portion, and the like are omitted from illustration. The bed shown in FIG. 5 is different from those of the above embodiments in that a light source 82 incorporating a power supply is arranged outside a bed 10, and light-transmitting means 84 comprising optical fibers or the like extend from the light source 82 and are connected to a lower stage portion 36 of a bed portion 34. An optical fiber sheet 81 obtained by bundling optical fibers and spreading the bundle like a sheet is placed on the lower stage portion 36. Since the optical fiber sheet 81 is uniformly distributed on the lower stage portion 36 of the bed portion 34, light is radiated to the human body more uniformly. As the optical fiber sheet 81, various types of sheets, e.g., an optical fiber pad fabricated by weaving optical fibers, can be used similarly. As the optical fiber pad that can be used in the present invention, U.S. Pat. No. 5,339,223, issued Aug. 16, 1994, is hereby incorporated by reference. The light source 82 converts the electric energy into the optical energy. With the arrangement of this embodiment, electrical insulation against the water 22 is increased.

Here, the number of the light source 82 is not limited to one. A plurality of light sources having different wavelengths may be used, and the light-transmitting means 84 may have a switching means for selecting either one of the plurality of light sources. In this case, in the same manner as in the embodiment described above, sterilization and synthesis of active vitamin D may be performed with near ultraviolet rays, and thereafter a light emitter for emitting infrared rays may be used in turn to perform a thermotherapy. Further, the light source need not be an artificial light source having a single wavelength, and natural light, e.g., sunlight, can also be used.

FIG. 6 is a schematic side sectional view showing a bed according to the forth embodiment of the present invention. In FIG. 6, a bed frame, a bed portion, and the like are omitted from illustration. As shown in FIG. 6, light emerging from the sun 86 may be condensed by a condensing portion 88, and the condensed light may be guided through a light-transmitting means 84, e.g., optical fibers, to an optical fiber sheet 81 arranged on the lower surface of a water bag 20. In this case, light rays having different wavelengths can be emitted simultaneously. Since a power supply is not used, the electrical charges can be economized.

The bed according to the embodiments described above is a so-called water bed. The fluid sealed in the bag constituting the bed is not limited to water. A transparent gas, e.g., an inert gas such as nitrogen, air, or an inert liquid, e.g., a perfluorocarbon solution, having excellent heat transmittance and electrical insulation can similarly be used to provide the same effect as described above.

As light is incident on the water bag 20, microbes proliferate in the water to change the transmittance of the water or to generate a gas. In order to prevent this, a preservative may be mixed in the water or near ultraviolet rays may be radiated to the water to suppress proliferation of the microbes in the water. The water in the water bag 20 can be forcibly circulated by a circulation pump and contamination of the water can be removed with a filter cartridge.

The light emitters need not be arranged on the lower surface of the water bag 20 but can be arranged on a side portion of the water bag 20. In this case, the side portion of the water bag 20 is constituted by a transparent member, and the lower surface of the water bag 20 is constituted by an opaque member.

As has been described above, according to the present invention, not only the bed user lying on the upper surface portion of the bed can sleep comfortably but also a bedsore caused by bacterial infection can be prevented since near ultraviolet rays can be radiated to the bed user. In other words, disinfection can be performed against bacteria present between the bed user and the bed. As a result, the number of times of disinfection done by the person in charge of nursing who attends to the bed-confined person as the bed user can be decreased.

When near ultraviolet rays are radiated to the bed user, active vitamin D, which cannot be synthesized in the human body but plays an important role in generation of the bone, can be generated. Thus, progress of osteoporosis can be suppressed. As the rays emerging from the light source, infrared rays may be used, so that the bed according to the present invention can be applied to a thermotherapy.

The present invention has the effect as described above not only to a bed-confined person but also to a person merely lacking in bone mass or rarely having an opportunity for a sunbath. Accordingly, the bed according to the present invention can be used for night-time sleeping, and even if a healthy person uses this bed, an excellent effect can be obtained.

When the light source is arranged in the drawer provided in the bed frame, the state of the light source can be observed easily, and the bed can be maintained easily.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

The basic Japanese Application No. 152667/1996 filed on Jun. 13, 1996 is hereby incorporated by reference.

What is claimed is:

1. A bed comprising:
    a bag filled with a transparent fluid, said bag being flexible at least at an upper surface portion thereof, and formed with a transparent portion on a lower surface portion of said bag and on an upper surface portion of said bag;
    a bed frame for holding said bag;
    a light source, provided on a lower surface of said bag and arranged outside of said bed frame, for emitting light;
    light-transmitting means for transmitting said light emitted from said light source to said lower surface of said bag;
    an optical fiber, arranged on said lower surface of said bag, for radiating said light emitted from said light-transmitting means into said bag;
    a power supply for supplying power to said light source,
    wherein said light emitted from said light source passes through said transparent fluid and propagates outside said bag through said transparent portion on said upper surface portion of said bag.

2. A bed according to claim 1, wherein said bed frame is provided with a drawer at a position corresponding to the lower surface of said bag, and said light source is arranged in said drawer.

3. A bed according to claim 1, further comprising temperature adjusting means for maintaining said fluid in said bag at a predetermined temperature.

4. A bed according to claim 1, wherein said light source is a light emitter for emitting near ultraviolet rays.

5. A bed according to claim 1, wherein said light source is a light emitter for emitting infrared rays.

6. A bed according to claim 1, wherein said light source comprises a plurality of light emitters for emitting light rays having a plurality of types of wavelengths.

7. A bed according to claim 6 further comprising switching means for performing switching among said plurality of light emitters as required.

8. A bed according to claim 1, wherein said fluid is water.

9. A bed according to claim 8 wherein a light-diffusing agent is dispersed in said water.

10. A bed according to claim 1, wherein said fluid is an inert gas.

11. A bed according to claim 1, wherein said fluid is an inert liquid.

12. A bed according to claim 1, wherein said bag is formed with a light-reflecting member on an inner side of a side portion thereof.

13. A bed comprising:

a bag filled with a transparent fluid, being flexible at least at an upper surface portion thereof, and formed with a transparent portion on an upper surface portion of said bag and on a lower surface portion of said bag;

a bed frame for holding said bag;

condensing means for condensing natural light; and light transmitting means for transmitting light condensed by said condensing means; and an optical fiber, arranged on a lower surface of said bag, for radiating said light transmitted from said light-transmitting means, wherein said light transmitted from said light transmitting means passes through said fluid and propagates outside said bag through said transparent portion on said upper surface portion of said bag.

* * * * *